(12) United States Patent
Vrignaud et al.

(10) Patent No.: US 8,388,963 B2
(45) Date of Patent: Mar. 5, 2013

(54) ANTITUMOR COMBINATIONS CONTAINING A VEGF-INHIBITING AGENT AND 5FU OR A DERIVATIVE THEREOF

(75) Inventors: Patricia Vrignaud, Combs la Ville (FR); Marielle Chiron-Blondel, Paris (FR); Marie-Christine Bissery, Charenton le Pont (FR); Eric Furfine, Croton on Hudson, NY (US); Jocelyn Holash, Yonkers, NY (US); Jesse M. Cedarbaum, Larchmont, NY (US)

(73) Assignees: Aventis Pharma SA, Antony (FR); Regeneron Pharmaceuticals Inc, Tarrytown, NY (US)

( * ) Notice: Subject to any disclaimer, the term of this patent is extended or adjusted under 35 U.S.C. 154(b) by 0 days.

(21) Appl. No.: 12/508,834

(22) Filed: Jul. 24, 2009

(65) Prior Publication Data

US 2009/0285841 A1 Nov. 19, 2009

Related U.S. Application Data

(63) Continuation of application No. 11/293,761, filed on Dec. 2, 2005, now abandoned.

(30) Foreign Application Priority Data

Dec. 3, 2004 (FR) ..................... 04 12870

(51) Int. Cl.
*A61K 38/18* (2006.01)
*C07K 14/71* (2006.01)
*C12N 15/62* (2006.01)

(52) U.S. Cl. ............. 424/134.1; 424/192.1; 514/1.1; 514/19.3; 514/21.2; 530/350

(58) Field of Classification Search ............. None
See application file for complete search history.

(56) References Cited

U.S. PATENT DOCUMENTS 7,354,579 B2 4/2008 Holash et al.

2004/0014667 A1 1/2004 Daly et al.
2005/0032699 A1 2/2005 Holash et al.

FOREIGN PATENT DOCUMENTS

WO WO 2005/000895 1/2005

OTHER PUBLICATIONS

Anon, et. al., Capecitabine/Bevacizumab Compared to Capecitabine Alone in Pretreated Metastatic Breast Cancer: Results of a Phase III Study, Clinical Breast Cancer; 3(6), pp. 375-377, 2003.
Braun, et. al., New Systemic Frontline Treatment for Metastatic Colorectal Carcinoma, Cancer, 2004; 100; pp. 1558-1577.
Feron, et. al., Targeting the Tumor Vascular Compartment to Improve Conventional Cancer Therapy, Trends in Pharmacological Sciences, 25(10); 2004; pp. 536-542.
Hurwitz, et. al., Bevacizumab Plus Irinotecan, Fluorouracil, and Leucovorin for Metastatic Colorector Cancer. N Engl J Med, 2004; 350(23): pp. 2335-2342.
Kabbinavar, et. al., Phase II, Randomized Trial Comparing Bevacizumab Plus Fluorouracil (FU)/Leucovorin (LV) With FU/LV Alone in Patients with Metastatic Colorectal Cancer, J of Clin Oncol; 2003; 21(1), pp. 60-65.
Kaklamani, et. al., Role of Capecitabine (Xeloda) in Breast Cancer, Expert Review of Anticancer Therapy, 3 (2), pp. 137-144, 2003.
Konner, et. al., Use of Soluble Recombinant Decoy Receptor Vascular Endothelial Growth Factor Trap (VEGF Trap) to Inhibit Vascular Endothelial Growth Factor Activity, Clinical Colorectal Cancer, 4(2); S81-S85; 2004.
Semela, et. al., Angiogenesis and Hepatocellular Carcinoma, Journal of Hepatology 41 (2004) pp. 864-880.
Keyomarsi, et. al., Folinic Acid Augmentation of the Effects of Fluoropyrimidines on Murine and Human Leukemic Cells, Cancer Research, vol. 46, pp. 5229-5235, (1986).
International Search Report for WO2006/059012 dated Jun. 8, 2006.

*Primary Examiner* — Christine J Saoud
*Assistant Examiner* — Jon M Lockard
(74) *Attorney, Agent, or Firm* — Sandra Brockman-Lee

(57) ABSTRACT

This invention relates to antitumor combinations comprising a VEGF inhibitor combined with 5-fluorouracil or with a 5-fluoropyrimidine derivative that are therapeutically useful in the treatment of neoplastic diseases, and pharmaceutical compositions comprising such combinations.

14 Claims, No Drawings

ANTITUMOR COMBINATIONS CONTAINING A VEGF-INHIBITING AGENT AND 5FU OR A DERIVATIVE THEREOF

The present invention relates to combinations of a VEGF inhibitor and a chemotoxic agent of the class of 5-fluorouracil or 5-fluoropyrimidines that are useful in the treatment of neoplastic diseases.

VEGF inhibitors, which are inhibitors of vascular endothelial growth factor, are, in the majority of cases, biological products chosen from soluble receptors, antisenses, RNA aptamers and antibodies. The 5-fluoropyrimidine derivatives are chosen from 5-fluorouracil, capecitabine or gemcitabine, which exhibit notable antitumoral and antileukemia properties; they are particularly useful in the treatment of ovarian cancer, breast cancer, lung cancer or colon cancer. The present combination is directed in particular toward the treatment of colon cancer or stomach cancer.

The description and the preparation of the VEGF inhibitor preferably used in the invention, which is a VEGF-Trap chimeric protein, is described in patent application WO00/75319. There are several embodiments of the chimeric protein. The embodiment corresponding to VEGF-Trap is that described in FIG. 24 (sequence; SEQ ID No: 1) in the patent application WO 00/75319. The VEGF-Trap used in the invention is a fusion protein comprising the VEGFR1 signal sequence fused to the Ig domain D2 of the VEGFR1 receptor, itself fused to the Ig domain D3 of the VEGFR2 receptor, in turn fused to the Fc domain of IgG1, also called VEGFR1R2-FcΔC1 or Flt1D2.Flk1D3.FcΔC1.

In general, the doses used, which depend on factors specific to the individual to be treated, are between 20 and 800 micrograms per kilo when the administration is carried out subcutaneously and from 2 to 20 micrograms per kilo when the administration is carried out intravenously or, optionally, intranasally at a lower dose of the order of 0.01 picogram to 1 mg per kilo.

The 5-fluorouracil is generally used intravenously at a dose of between 500 mg/m$^2$ and 5000 mg/m$^2$ per week; as regards the 5-fluoropyrimidine derivatives such as capecitabine, they are generally used, for the latter, orally at a dose of between 500 and 3000 mg/m$^2$ generally administered in two daily doses. Gemcitabine is generally used intravenously at a dose of between 500 and 2000 mg/m$^2$ per week.

An article by H Hurwitz, L Fehrenbacher, W Novotny, T Cartwright, J Hainsworth, W Heim, J Berlin, A Baron, S Griffing, E Holmgren, N Ferrara, G Fyfe, B Rogers, R Ross, F Kabbinavar published in "The New England Journal of Medicine" (*N. Eng. J. Med.* 350 (23) Jun. 3, 2004, 2335-2352) has described a clinical trial proving a better survival rate when the combination of bevacizumab with irinotecan, 5FU and leucovorin is used compared with the same combination containing no bevacizumab. Nothing proves, in this clinical trial, that the improvement in survival rate comes from the combination of 5FU with the bevacizumab; it may just as well come from the combination of irinotecan or of leucovorin with the bevacizumab, or may come from the quadruple combination. Now, as it is known that each of the anticancer agents brings, along with its therapeutic effect, toxic side effects, it appears to be opportune to limit their presence as much as possible, especially when the same effect can be obtained in the absence of at least one of them. In the present case, it is known that irinotecan leads to considerable diarrhea, which has sometimes led to the treatment having to be stopped. Furthermore, this article does not prove any synergistic effect within Corbett's meaning, i.e. an effect that cannot be obtained with each of the elements of the combination used alone at its maximum tolerated dose.

It has now been found, and it is this that forms the subject of the present invention, that the effectiveness of VEGF inhibitors can be considerably improved when they are administered in combination with at least one substance therapeutically useful in anticancer treatments that has a mechanism of action different from that of the VEGF inhibitors.

Moreover, since the activity of the products depends on the doses used, it is possible to use higher doses and to increase the activity by decreasing the phenomena of toxicity or delaying their appearance through the combination with the VEGF inhibitors or with their analogs of other therapeutically active substances, of growth factors of hematopoietic type, such as G-CSF or GM-CSF, or certain interleukins.

More particularly, the invention relates to the combinations of VEGF-Trap with 5-fluorouracil or derivatives thereof such as capecitabine or gemcitabine. It also relates to the combinations also including folinic acid generally combined with 5-FU.

The improved effectiveness of a combination according to the invention can be demonstrated by determining the therapeutic synergism.

A combination shows therapeutic synergism if it is therapeutically superior to one or other of the constituents used at its optimum dose [T. H. Corbett et al., Cancer Treatment Reports, 66, 1187 (1982)].

In order to demonstrate the effectiveness of a combination, it may be necessary to compare the maximum tolerated dose of the combination with the maximum tolerated dose of each of the individual constituents in the study under consideration. This effectiveness can be quantified, for example by the $\log_{10}$ of the killed cells, which is determined according to the following formula:

$$\log_{10} \text{killed cells} = T - C(\text{days})/3.32 \times T_d$$

in which T–C represents the delay in growth of the cells, which is the average time, in days, for the tumors of the treated group (T) and the tumors of the control group (C) to reach a predetermined value (1 g, for example) and $T_d$ represents the time, in days, required for the volume of the tumor to double in the control animals [T. H. Corbett et al., Cancer, 40, 2660.2680 (1977); F. M. Schabel et al., Cancer Drug Development, Part B, Methods in Cancer Research, 17, 3-51, New-York, Academic Press Inc. (1979)]. A product is considered to be active if $\log_{10}$ killed cells is greater than or equal to 0.7. A product is considered to be very active if the $\log_{10}$ killed cells is greater than 2.8.

The combination, used at its own maximum tolerated dose, in which each of the constituents will be present at a dose generally less than or equal to its maximum tolerated dose, which show therapeutic synergy when the $\log_{10}$ killed cells is greater than the value of $\log_{10}$ killed cells of the best constituent when it is administered alone.

The effectiveness of the combinations on solid tumors can be determined experimentally in the following way:

30 to 60 mg of an MC 13/C mammary tumor fragment are transplanted bilaterally, subcutaneously, into the animals subjected to the experiment, generally mice, on day 0. The animals bearing the tumors are randomized before being subjected to the various treatments and controls. In the case of treatment of advanced tumors, the tumors are left to develop until the desired size, the animals having insufficiently developed tumors being eliminated. The animals selected are divided up randomly so as to undergo the treatments and the controls. Animals not bearing tumors can also be subjected to the same treatments as the tumor-bearing animals in order to be able to dissociate the toxic effect from the actual effect on the tumor. The chemotherapy generally begins from 3 to 22 days after the tumor transplant, according to the type of tumor, and the animals are observed every day. The various groups of animals are weighed three or four times a week until the maximum weight loss is obtained, and then the groups are weighed at least once a week until the end of the trial.

The tumors are measured two or three times a week until the tumor reaches approximately 2 g or until the animal's death if the latter occurs before the tumor reaches 2 g. The animals are autopsied when they are sacrificed.

The antitumor activity is determined as a function of the various parameters recorded.

To study the combinations on leukemias, a given number of cells are transplanted into the animals and the antitumor activity is determined by the increase in survival time of the treated mice compared with the controls. A product is considered to be active if the increased survival time is greater than 27% and it is considered to be very active if it is greater than 75% in the case of P388 leukemia.

By way of examples, the following tables give the results obtained with combinations of VEGF-Trap and 5-fluorouracile used at their optimum dose.

The present invention also relates to the pharmaceutical compositions containing the combinations according to the invention.

The products that constitute the combination can be administered simultaneously, separately or spread out over time so as to obtain the maximum effectiveness of the combination; it being possible for each administration to have a variable duration ranging from complete rapid administration to continuous infusion.

It results therefrom that, for the purpose of the present invention, the combinations are not only limited to those which are obtained by physical combination of the constituents, but also to those which allow a separate administration which may be simultaneous or spread out over time.

The compositions according to the invention are preferably compositions that can be administered parenterally. However, these compositions may be administered orally.

The compositions for parenteral administration are generally sterile pharmaceutically acceptable solutions or suspensions which may optionally be prepared extemporaneously at the time of use. For the preparation of nonaqueous solutions or suspensions, natural plant oils such as olive oil, sesame oil or paraffin oil or injectable organic esters such as ethyl oleate can be used. The aqueous sterile solutions may consist of a solution of the product in water. The aqueous solutions are suitable for intravenous administration insofar as the pH is suitably adjusted and isotonicity is effected, for example by means of a sufficient amount of sodium chloride or glucose. The sterilization can be carried out by heating or by any other means that does not impair the composition. The combinations may also be in the form of liposomes or in the form of a combination with carriers such as cyclodextrins or polyethylene glycols.

In the combinations according to the invention, the application of these constituents may be simultaneous, separate or spread out over time, it is particularly advantageous for the amount of VEGF-Trap derivative to represent from 2 to 80% by weight of the combination, it being possible for this content to vary according to the nature of the substance combined, to the desired effectiveness and to the nature of the cancer to be treated.

"Pharmaceutically effective amount" is meant to describe an amount of the combinations according to the present invention, and constituents thereof, effective in producing the desired therapeutic effect. The constituents of the combinations according to the invention may be administered in dosages which are pharmaceutically effective for each constituent, or in dosages which are sub-clinical, i.e., less than pharmaceutically effective for each, or a combination thereof, provided that the combined dosages are pharmaceutically effective.

The combinations according to the invention are particularly useful in the treatment of colon and/or stomach cancers. In particular, they may have the advantage of being able to use the constituents at doses that are much lower than those at which they are used alone.

The following example illustrates a combination according to the invention.

EXAMPLE

Ampoules of 1 cm$^3$ containing 25 mg of VEGF-Trap, which are diluted in a phosphate buffer, are prepared, according to the usual technique, for subcutaneous administration.

0.2 ml per mouse is prepared, according to the usual technique, for intravenous administration, from a commercial solution of 5 cm$^3$ containing 250 mg of 5 FU to be diluted with 5% glucose in water.

These solutions are administered simultaneously, after suitable dilution, by infusion.

The treatment can be repeated several times per day or per week until partial or complete remission or recovery.

| Dosage in mg/kg/day (total dose in mg/kg) | | | | | | |
|---|---|---|---|---|---|---|
| sc VEGF-Trap (day 4, 7, 11, 14, 18, 21) | iv 5-FU (day 4, 11, 18) | Death due to the treatment | % weight loss at the lowest point | % T/C | T-C days | lck |
| 40 (240) | — | 0/5 | 2.3 | 4 | 12.7 | 1.4 |
| 25 (150) | — | 0/5 | 1.1 | 8 | 13.9 | 1.5 |
| 10 (60) | — | 0/5 | 1.1 | 9 | 12.1 | 1.3 |
| 2.5 (15) | — | 0/5 | 0.9 | 32 | 5.2 | 0.6 |
| — | 145 (435) | 1/5 | 8.7 | Toxic | — | — |
| — | 90 (270) | 0/5 | 4.8 | 0 | 12.5 | 1.3 |
| — | 55.8 (167.4) | 0/5 | 1.1 | 12 | 7.8 | 0.8 |
| — | 34.6 (103.8) | 0/5 | +2.3 | 34 | 4.6 | 0.5 |
| 40 (240) | 90 (270) | 0/5 | 8.0 | 0 | 25.2 | 2.7 |
| 25 (150) | 90 (270) | 0/5 | 9.6 | 0 | 24.8 | 2.7 |
| 10 (60) | 90 (270) | 0/5 | 7.4 | 0 | 23.1 | 2.5 |
| 10 (60) | 55.8 (167.4) | 0/5 | 4.4 | 0 | 16.5 | 1.8 |
| 10 (60) | 34.6 (103.8) | 0/5 | 5.4 | 1 | 20.0 | 2.2 |
| 2.5 (15) | 90 (270) | 0/5 | 7.0 | 0 | 20.4 | 2.2 |
| 2.5 (15) | 55.8 (167.4) | 0/5 | 2.0 | 0 | 18.0 | 1.9 |
| 2.5 (15) | 34.6 (103.8) | 0/5 | 2.0 | 6 | 11.7 | 1.3 |

BCM-1428 (May 28, 2004-Jul. 30, 2004): tumor doubling time = 2.8 days. Average time for 750 mg on controls = 22.2 d. Treatment period = 18 d for VEGF-Trap and combination, and 15 days for 5-FU.
Abbreviations used:
T/C = inhibition of tumor growth at day 24,
(T-C) delay of tumor growth,
lck = log cells killed.

SEQUENCE LISTING

<160> NUMBER OF SEQ ID NOS: 1

<210> SEQ ID NO 1
<211> LENGTH: 458
<212> TYPE: PRT
<213> ORGANISM: Artificial
<220> FEATURE:
<223> OTHER INFORMATION: VEGFR1R2-Fc(delta)C1(a)

<400> SEQUENCE: 1

```
Met Val Ser Tyr Trp Asp Thr Gly Val Leu Leu Cys Ala Leu Leu Ser
1               5                   10                  15

Cys Leu Leu Leu Thr Gly Ser Ser Gly Ser Asp Thr Gly Arg Pro
                20                  25                  30

Phe Val Glu Met Tyr Ser Glu Ile Pro Glu Ile Ile His Met Thr Glu
                35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
                100                 105                 110

Leu Tyr Lys Thr Asn Tyr Leu Thr His Arg Gln Thr Asn Thr Ile Ile
            115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350
```

-continued

| | | | | | | | | | | | | |
|---|---|---|---|---|---|---|---|---|---|---|---|---|
| Gln | Pro | Arg<br>355 | Glu | Pro | Gln | Val | Tyr<br>360 | Thr | Leu | Pro | Pro<br>365 | Ser | Arg | Asp | Glu |
| Leu | Thr<br>370 | Lys | Asn | Gln | Val | Ser<br>375 | Leu | Thr | Cys | Leu<br>380 | Val | Lys | Gly | Phe | Tyr |
| Pro<br>385 | Ser | Asp | Ile | Ala | Val<br>390 | Glu | Trp | Glu | Ser | Asn<br>395 | Gly | Gln | Pro | Glu | Asn<br>400 |
| Asn | Tyr | Lys | Thr | Thr<br>405 | Pro | Pro | Val | Leu | Asp<br>410 | Ser | Asp | Gly | Ser | Phe<br>415 | Phe |
| Leu | Tyr | Ser | Lys<br>420 | Leu | Thr | Val | Asp | Lys<br>425 | Ser | Arg | Trp | Gln | Gln<br>430 | Gly | Asn |
| Val | Phe | Ser<br>435 | Cys | Ser | Val | Met | His<br>440 | Glu | Ala | Leu | His | Asn<br>445 | His | Tyr | Thr |
| Gln | Lys<br>450 | Ser | Leu | Ser | Leu | Ser<br>455 | Pro | Gly | Lys | | | | | | |

We claim:

1. A method of treating colon cancer, in a patient in need of such treatment, comprising administering to the patient a pharmaceutically effective amount of a combination of VEGF-Trap, 5-fluorouracil, and folinic acid, wherein the VEGF-Trap comprises the amino acid sequence of SEQ ID NO:1.

2. The method according to claim 1 wherein the VEGF-Trap is administered in an amount of 2% to 80% by weight of the total weight of VEGF-Trap and 5-fluorouracil.

3. The method according to claim 1, wherein the amounts of the VEGF-Trap, 5-fluorouracil, and folinic acid administered exhibit a therapeutically synergistic effect in the treatment of colon cancer.

4. The method according to claim 1, wherein the combination effects a $\log_{10}$ cell kill of at least 1.8.

5. The method according to claim 1, wherein the combination effects a $\log_{10}$ cell kill of at least 2.2.

6. The method according to claim 1, wherein the combination effects a $\log_{10}$ cell kill of at least 2.5.

7. The method according to claim 1, wherein the combination effects a $\log_{10}$ cell kill of at least 2.7.

8. A method of treating stomach cancer, in a patient in need of such treatment, comprising administering to the patient a pharmaceutically effective amount of a combination of VEGF-Trap, 5-fluorouracil, and folinic acid, wherein the VEGF-Trap comprises the amino acid sequence of SEQ ID NO:1.

9. The method according to claim 8, wherein the VEGF-Trap is administered in an amount of 2% to 80% by weight of the total weight of VEGF-Trap and 5-fluorouracil.

10. The method according to claim 8, wherein the amounts of the VEGF-Trap, 5-fluorouracil and folinic acid administered exhibit a therapeutically synergistic effect in the treatment of stomach cancer.

11. The method according to claim 8, wherein the combination effects a $\log_{10}$ cell kill of at least 1.8.

12. The method according to claim 8, wherein the combination effects a $\log_{10}$ cell kill of at least 2.2.

13. The method according to claim 8, wherein the combination effects a $\log_{10}$ cell kill of at least 2.5.

14. The method according to claim 8, wherein the combination effects a $\log_{10}$ cell kill of at least 2.7.

* * * * *